United States Patent [19]
Tury et al.

[11] Patent Number: 5,184,017
[45] Date of Patent: Feb. 2, 1993

[54] METHOD AND APPARATUS FOR DETECTING A COMPONENT GAS IN A SAMPLE

[75] Inventors: Edward L. Tury, Brighton, Mich.; Keith Kaste; Ross E. Johnson, both of San Luis Obispo, Calif.; David O. Danielson, Gregory, Mich.

[73] Assignee: Sensors, Inc., Saline, Mich.

[21] Appl. No.: 746,939

[22] Filed: Aug. 19, 1991

Related U.S. Application Data

[62] Division of Ser. No. 406,041, Sep. 12, 1989, Pat. No. 5,060,505.

[51] Int. Cl.[5] .............................................. G01N 21/61
[52] U.S. Cl. .............................. 250/343; 250/252.1; 250/339
[58] Field of Search ........ 73/1 G, 23.21, 23.22-23.29; 250/343, 340, 341, 344, 345, 346, 339, 349, 252.1 R, 252.1 A

[56] References Cited

U.S. PATENT DOCUMENTS

| | | | |
|---|---|---|---|
| 2,718,597 | 9/1955 | Heigl et al. | 250/252.1 A |
| 3,465,143 | 9/1969 | Doonan | 250/339 |
| 3,790,797 | 2/1974 | Sternberg | 250/345 |
| 3,812,330 | 5/1974 | Bowman et al. | 235/92 |
| 3,860,818 | 1/1975 | Stalder et al. | 250/343 |
| 3,887,473 | 6/1975 | Sternberg et al. | 250/345 |
| 3,898,462 | 8/1975 | Ishida et al. | 250/344 |
| 3,904,880 | 9/1975 | Benz et al. | 250/343 |
| 3,923,403 | 12/1975 | Harklau | 356/201 |
| 4,010,368 | 3/1977 | Pelta | 250/343 |
| 4,013,260 | 3/1977 | McClatchie et al. | 250/343 |
| 4,069,420 | 1/1978 | Ross | 250/341 |
| 4,346,296 | 8/1982 | Passaro et al. | 250/343 |
| 4,370,553 | 1/1983 | Waycaster et al. | 250/343 |
| 4,423,739 | 1/1984 | Passaro et al. | 128/719 |
| 4,480,190 | 10/1984 | Burough et al. | 356/437 X |
| 4,673,812 | 6/1987 | Yoneda | 250/252.1 |
| 4,678,914 | 7/1987 | Melrose et al. | 250/343 |
| 4,687,934 | 8/1987 | Passaro et al. | 250/343 |
| 4,849,637 | 7/1989 | Cerff et al. | 250/344 X |
| 4,850,697 | 7/1989 | Schoennauer et al. | 356/419 |
| 4,914,719 | 4/1990 | Conlon et al. | 250/339 |
| 4,918,311 | 4/1990 | Rogers | 250/343 |
| 5,013,920 | 5/1991 | Asono et al. | 250/343 |
| 5,060,505 | 10/1991 | Tury et al. | 73/1 G |

FOREIGN PATENT DOCUMENTS

| | | | |
|---|---|---|---|
| 142232 | 7/1985 | Japan | 250/252.1 A |
| 274844 | 11/1988 | Japan | 250/252.1 |
| 2089993 | 6/1982 | United Kingdom | 250/252.1 A |

OTHER PUBLICATIONS

TMM Capnometer Model 2000 Operators Manual, 1984 pp. 1-32.
Burr-Brown "10MH$_2$ Analog Multiplier Carriers Output Amp, Breaks Bandwidth Barrier", Jul. 1986, pp. 1-5.

*Primary Examiner*—Tom Noland
*Attorney, Agent, or Firm*—Price, Heneveld, Cooper, Dewitt & Litton

[57] ABSTRACT

A non-dispersive infrared gas analyzer especially adapted for measuring the concentrations of HC, CO and $CO_2$ in a vehicle exhaust includes a sample chamber for holding a sample gas, a radiation emitter for directing a beam through the chamber and a detector for indicating the amount of radiation absorbed. A plurality of filters each of which transmit radiation at an absorption band of a gas component to be detected are alternatingly positioned in the radiation path to produce a time-multiplexed signal having concentration information for all gases. The time-multiplexed detector output is corrected for gain and offset errors "on-the-fly", without requiring demultiplexing, through the use of an analog multiplier circuit. The correction factors are themselves determined without demultiplexing the detector output signal.

16 Claims, 14 Drawing Sheets

FIG. 9

METHOD AND APPARATUS FOR DETECTING A COMPONENT GAS IN A SAMPLE

This is a division of application Ser. No. 07/406,041, filed Sep. 12, 1989, and now U.S. Pat. No. 5,060,505.

BACKGROUND OF THE INVENTION

This invention relates to gas analyzers. In particular, the invention concerns non-dispersive infrared gas analyzers. The invention is especially adapted for measuring the concentration of gas components in vehicle exhaust gas.

Non-dispersive Infrared (IR) gas analyzers utilize an IR source to direct IR radiation through a mixture of gases contained in a sample chamber. The IR energy is passed through the mixture in the sample chamber at absorption frequencies for gases whose concentration is to be determined. The detected absorption at each frequency is indicative of the concentration of the component gas having the particular absorption band. In the particular application to automotive gas analyzers, the gases whose concentrations are of interest include HC (hydrocarbons), CO and $CO_2$. In order to measure the concentration of these gases, multiple light filters, having transmission bands at an absorption band for each component gas, are alternatingly placed between the source and detector to provide an indication for each gas. The detector output is a single, time-multiplexed signal which contains information for all component gas concentrations. This signal is conventionally demultiplexed into individual signals and applied to separate amplifier channels for each gas component.

To produce accurate readings of automotive exhaust gases, the system must be calibrated frequently in order to make adjustments for drift in the components as well as for the buildup of exhaust particles on surfaces of optical components. Because of the significant decreases in allowed vehicle emission of pollutants, more sensitive and accurate measurements are required. At least one state now requires that the gain of each gas-measurement channel be calibrated at a minimum of two points with respect to full scale, or 100% span. For example, the two calibration points may be at 20% and 60% of full scale. Overall performance of the gas analyzer must be superior to meet these requirements, as well as those that are likely to be imposed in the future.

The output of each gas channel additionally has a tendency to drift due to temperature variations, component aging and other factors. This drift, or offset, must be cancelled, or zeroed, in order to avoid false readings. Because each gas measuring channel must be individually zeroed, the required effort, and chances for error, are multiplied. While automated, self-zeroing schemes have been proposed, such schemes typically merely automate functions that were previously manually performed. The result is yet a further complication of the hardware and increased chances for error.

SUMMARY OF THE INVENTION

The present invention provides a method and apparatus for detecting a component gas in a gas sample. The invention is embodied in an apparatus having a sample chamber for containing a sample gas including the component gas to be detected. A source is provided for directing infrared radiation through the sample chamber in a preselected spectrum band. A detector responsive to radiation incident thereon in the pre-selected spectra band, that has passed through the sample chamber from the source, for producing a detector output. A signal processing means is provided that is responsive to the detector output for indicating the relative concentration of the component gas(es) to be detected.

The signal processing means, according to one aspect of the invention includes multiplexing means for imposing a plurality of filters during distinct time intervals between the source and the detector to time multiplex the detector output. One of the filters has radiation transmitting characteristics that will provide an indication of the concentration of the component gas to be detected. Additionally, a correction circuit is provided that is adapted to applying a correction factor to the detector output to provide a corrected output. The correction circuit is synchronized with the multiplexing means in order to apply a correction factor to the detector output for the component gas to be detected during the interval of time that the filter having the transmitting characteristics of the component gas to be detected is between the source and the detector means.

According to another aspect of the invention, the signal processing means includes a circuit having first and second inputs and adapted to producing a difference output that is the difference between a signal provided to the first input and a signal provided to the second input. A first means is provided for applying the detector output to the first input and a zero-value signal to the second input, with substantially nonabsorbent gas filling the sample chamber, to produce an offset value on the difference output. Additionally, a second means is provided for applying the detector output to the first input and the offset value to the second input, with a sample gas filling the sample chamber, to thereby produce a difference output that indicates the relative concentration of the component gas in the sample gas.

The circuit means may additionally include a third input. The difference output of the circuit means is, then, the sum of a signal applied to the third input and the difference between a signal applied to the first input and a signal to the second input. A third means may be provided for applying the detector output to the first input and the offset value to the second input, with a nonabsorbent gas filling the sample chamber, to produce a trim value on the difference output. The trim value is applied to the third input to produce the difference output when a sample gas is filling the sample chamber. This provides enhanced accuracy of the difference output that indicates the relative concentration of the component gas in the sample gas.

A method, according to the invention, includes imposing a plurality of filters during distinct time intervals in the path of the radiation to time-multiplex the detector signal. One of the filters has radiation transmitting characteristics that will provide an indication of the concentration of the component gas to be detected. A correction signal is applied to the detector signal in synchronism with the imposing of the filters to apply a correction factor to the detector output for the component gas to be detected during the interval of time that the filter having the radiation transmitting characteristics of the component gas to be detected is in the infrared radiation passing through the sample chamber and thereby providing a corrected detector signal.

These and other objects, advantages and features of this invention will become apparent upon review of the following specification in conjunction with the drawings.

DESCRIPTION OF THE PREFERRED EMBODIMENT

Figure 1:
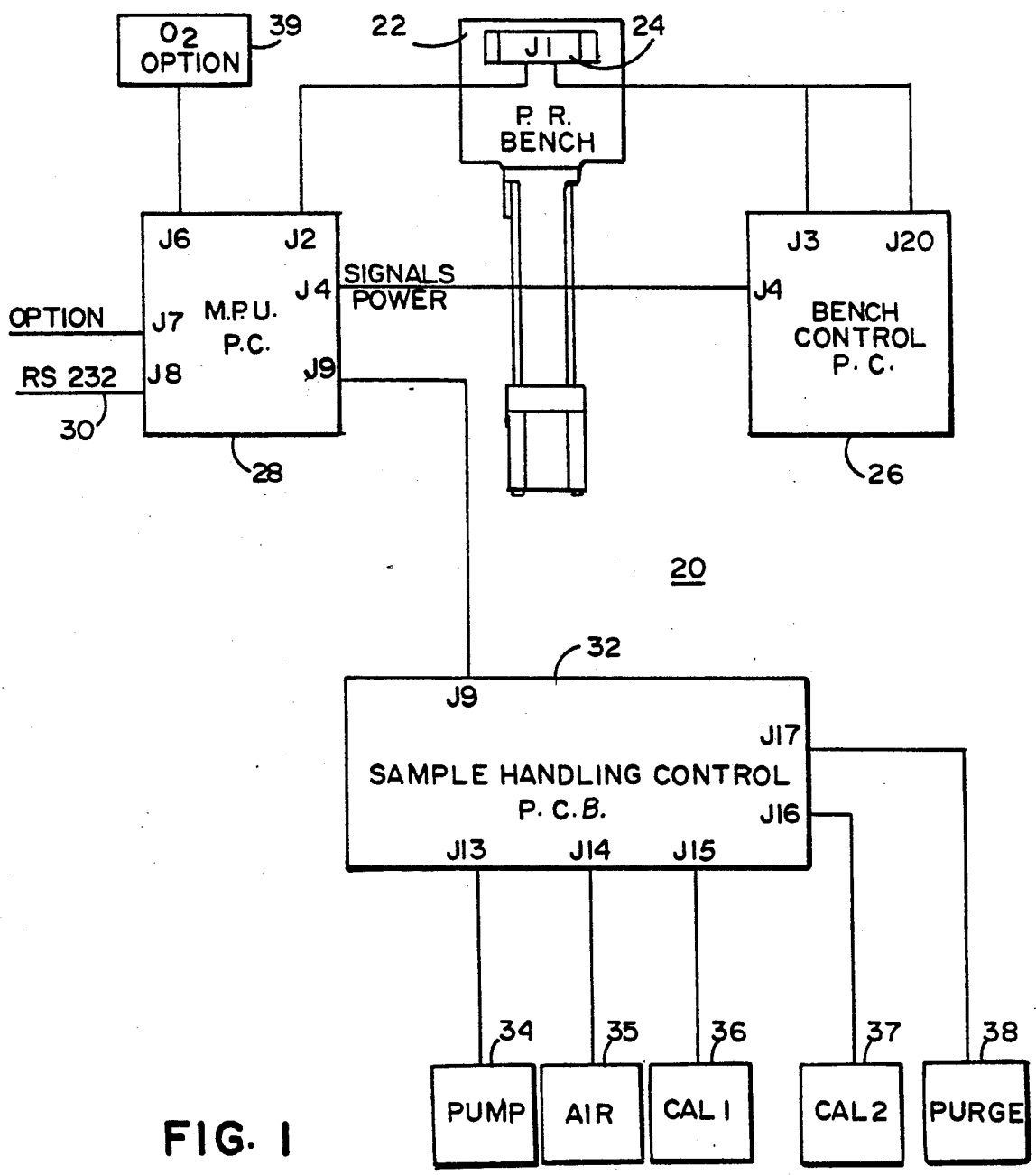
FIG. 1 is a block diagram of a gas analyzer system according to the invention.

Referring now specifically to the drawings, and the illustrative embodiments depicted therein, a non-dispersive infrared gas analyzer system 20 includes an optical bench unit 22 interconnected through a connector 24 to a bench control unit 26 for controlling certain functions occurring within the bench unit. System 20 further includes a microprocessor unit 28 for also controlling certain functions of bench unit 22 as well as communications with a host computer (not shown) through an RS232 serial communication port 30 (FIG. 1). Microprocessor unit 28 additionally coordinates the functions of a sample handling control unit 32 which, in turn, coordinates the functioning of control devices 34–38 in order to provide the proper gases at the appropriate times to the optical unit 22. In particular, control unit 32 controls the operation of a pump switch 34 in order to supply either a sample gas, whose HC, CO, $CO_2$ components are to be determined, or ambient air to bench unit 22. An air solenoid 35 operates a valve which determines whether pump 34 will be providing the sample gas or ambient air to the unit. CAL1 and CAL2 solenoid valves 36, 37 are energized to provide, separately, two standard calibration gases during a routine calibration of the system 20 using calibrating gas. The two gas mixtures provide separate concentrations of the component gases in order to provide two-point calibration. A purge switch 38 energizes a vacuum pump to remove sample gas from the optical unit 22 after a test. Microprocessor unit 28 is additionally adapted to accommodate various optional equipment such as an $O_2$ sensor 39 to monitor the $O_2$ content of the sample gas in the sample chamber through techniques other than IR gas analysis.

Figure 2:
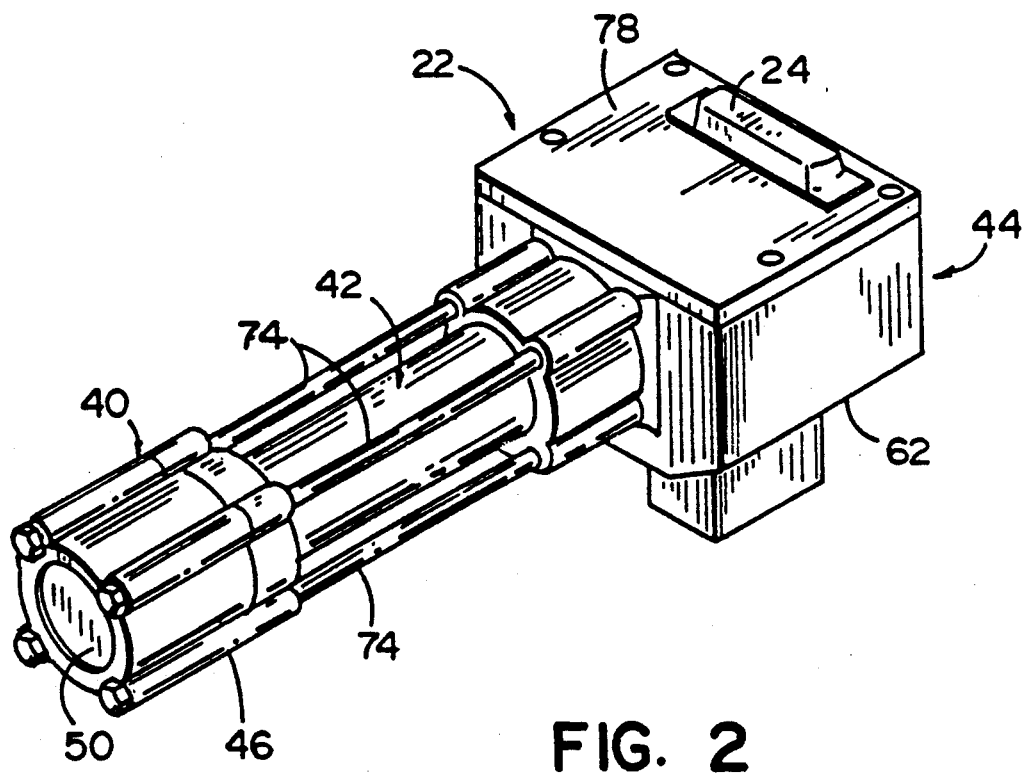
FIG. 2 is a perspective view of an optical bench unit.
Figure 4:
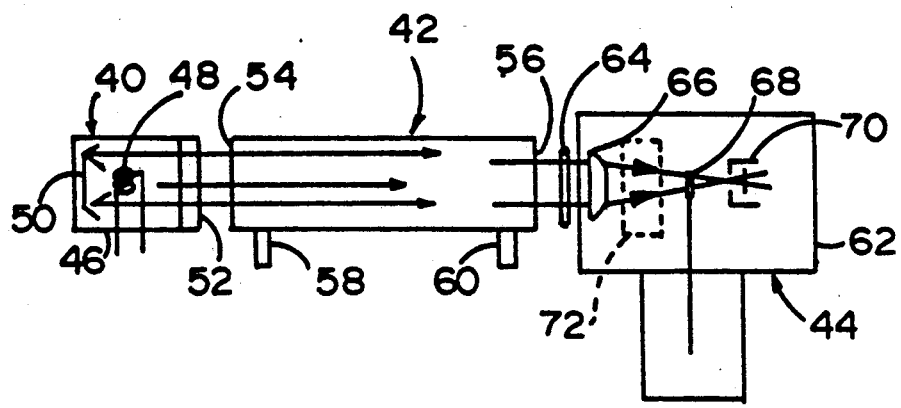
FIG. 4 is a schematic diagram of the optical path through an optical bench unit.

Optical bench unit 22 includes a source module 40, a sample chamber 42 and a receiver module 44 (FIGS. 2 and 4). Source module 40 includes a housing 46 which surrounds and hermetically encloses an infrared source 48 made from Kanthal Al alloy wire. Infrared radiation from source 48 is reflected by a spherical mirror 50 through a window 52 which seals an opening in housing 46. Sample chamber 42 is a hollow tubular member having open ends 54, 56. Sample chamber 42 additionally includes inlet and outlet gas ports 58, 60 for circulating gas through the sample chamber.

Receiver module 44 includes a hermetically-sealed housing 62 having an opening aligned with chamber 42 and covered by a calcium fluoride window 64 through which, IR radiation enters the interior of housing 62. The radiation passing through window 64 is focused by a silicone plano-convex lens 66, then passes through a radiation chopper assembly 68 and finally to a radiation detector 70, made from lead selenide. A calibration assembly 72 in housing 62 is selectively positioned in the path of the IR radiation, as will be set forth in more detail below. During gas measurement, however, calibration assembly 72 is effectively removed from the radiation path.

The structure of optical unit 22 provides exceptional ease of cleaning contamination from the exhaust gases passing through sample chamber 42. Sample chamber 42 is open at opposite ends 54, 56 which, are respectively closed by window 52 of the source module and window 64 of the receiver module, when the unit is assembled. The optical surfaces of windows 52, 64 may be readily cleaned of contamination by removing a plurality of elongated fasteners 74 extending from the source module to the receiver module around the sample chamber. This allows the source and receiver modules to be readily separated from the sample chamber to expose the contaminated optical surfaces. Cleaning is a matter of swabbing the very accessible interior of sample chamber 42 and wiping windows 52, 64. The unit may then be easily reassembled by replacing fasteners 74.

Figure 3:
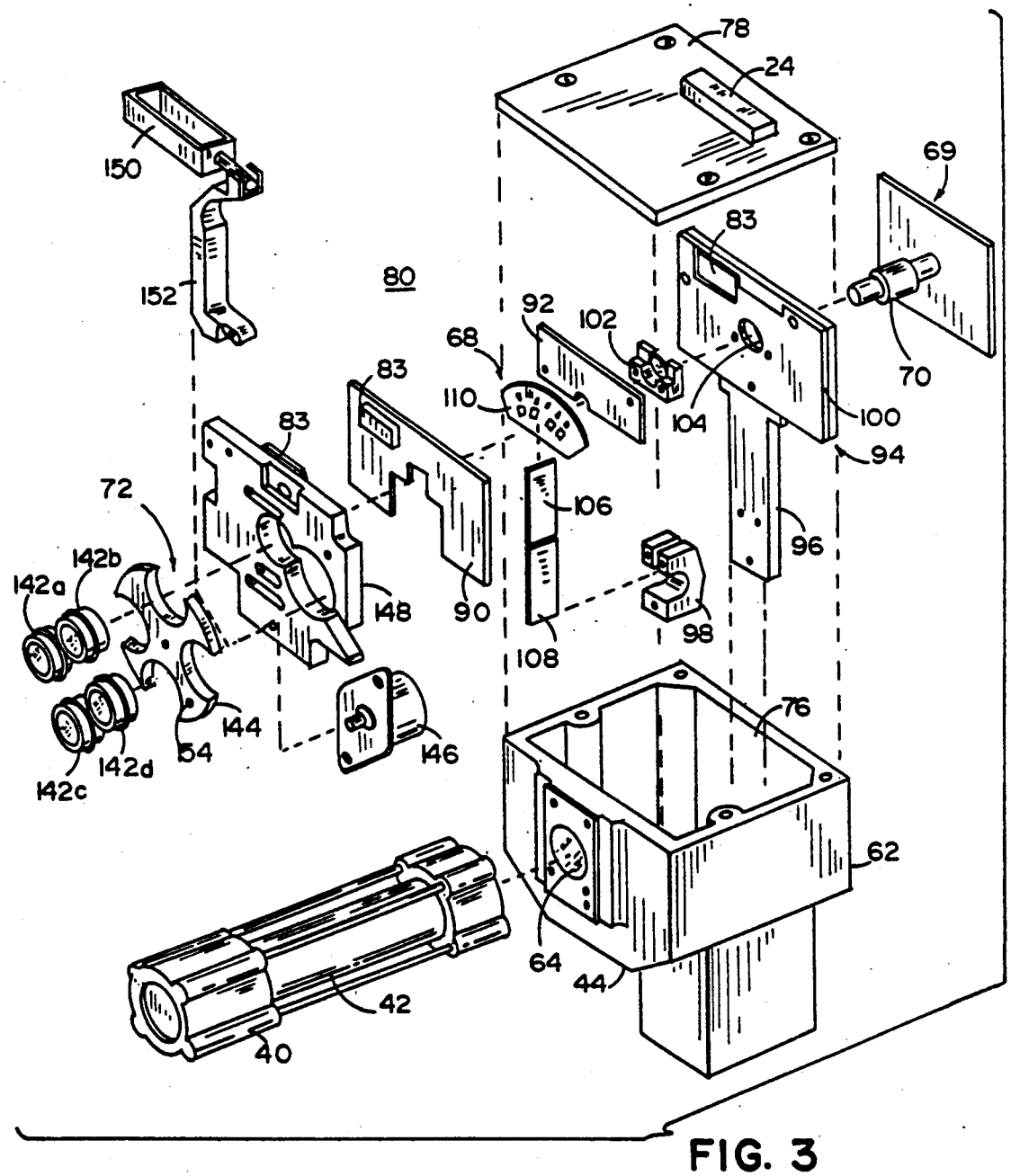
FIG. 3 is an exploded perspective view of the optical bench showing the components of the radiation detection subassembly.
Figure 5:
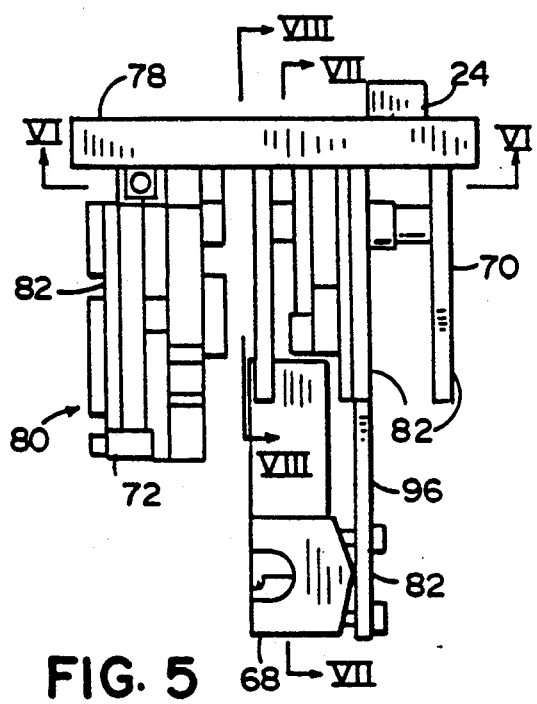
FIG. 5 is a side view of the removable portion of the radiation detector subassembly.

Housing 62 of receiver module 44 includes an access opening 76 closed by an access cover 78 (FIG. 3). The internal components of receiver module 44 are mounted to access cover 78 forming a radiation detection subassembly 80 which is removable as a unit from housing 62 merely by removing cover 78 (FIGS. 3 and 5). Detection subassembly 80 includes a plurality of electromechanical modules, generally illustrated at 82, which are electrically interconnected through connectors 83 which engage mating connectors 85 on an interconnection circuit board 84 mounted to bottom side 86 of cover 78. A plurality of tabs 88, extending from cover 78, provide mechanical attachment for the electromechanical modules 82.

By reference to FIG. 3, the electromechanical modules include, in order of sequence along the radiation path, a calibration assembly 72, a synchronizing-source circuit board 90, a radiation chopper assembly 68, a synchronizing-detector circuit board 92 and a radiation detector and pre-amplifier assembly 69. A fiberglass support member 94, attached to access cover 78, includes a lower extension 96 to which a bracket 98, for mounting chopper assembly 68, is attached. A sheet 100 of metallic material is mounted on a forward surface of support member 94 and provides a thermal mass to assist in the thermal stabilization of the interior of the receiver module. Radiation detector and pre-amplifier assembly 69 attaches to the surface of support member 94 opposite sheet 100. A bracket 102 attached to sheet 100 receives the forward portion of a detector 70 which is mounted to radiation detector and pre-amplifier assembly 69 and traverses an opening 104 in support member 94. Sync-detector board 92 mounts to sheet 100 over bracket 102. Radiation chopper assembly 68 is positioned forward of sync-detector board 92.

Figure 7:
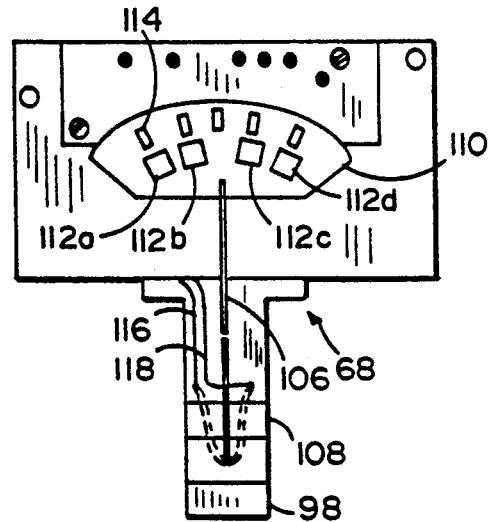
FIG. 7 is a front view of the piezoelectric chopper assembly taken along VII—VII in FIG. 5.
Figure 6:
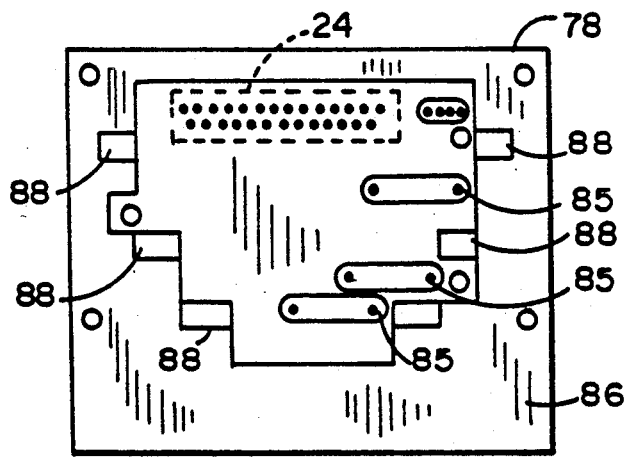
FIG. 6 is a bottom view taken along VI—VI in FIG. illustrating the bottom of the access cover and the interconnecting circuit board.
Figure 8:
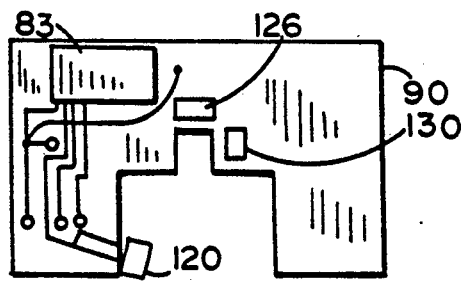
FIG. 8 is a front view of a sensor circuit board assembly taken along the lines VIII—VIII in FIG. 5.

Chopper assembly 68 includes a piezoelectric (PE) blade 106 supported at one end 108 in bracket 98 (FIGS. 3 and 7). A planar, arc-shaped filter carrier 110 is mounted at an opposite end of blade 106 and includes a plurality of radiation filters 112 which each individually transmits radiation at an absorption band of one of the gases HC, CO and $CO_2$. A fourth filter is provided as a reference filter. A plurality of openings 114 are angularly spaced along the upper edge of filter carrier 110 to generate indexing marks or pulses. Such a piezoelectric chopper assembly is disclosed in U.S. Pat. No. 4,850,697, issued to Larry Schoennauer et al for a RESONANT PIEZOELECTRIC CHOPPER FOR INFRARED RADIATION, and assigned to the present assignee, the detailed description of which is hereby incorporated herein by reference and will not be repeated. Suffice it to say that PE blade 106 vibrates in resonance with the assistance of suitably-applied signals on leads 116, 118. Because end 108 is fixed, the vibration of blade 106 causes filters 112$a$–112$d$ to pass alternatingly in front of the radiation light path. In this manner, the IR radiation that is passed through the sample gas is alternatingly filtered by filters 112$a$–112$d$.

Figure 9:
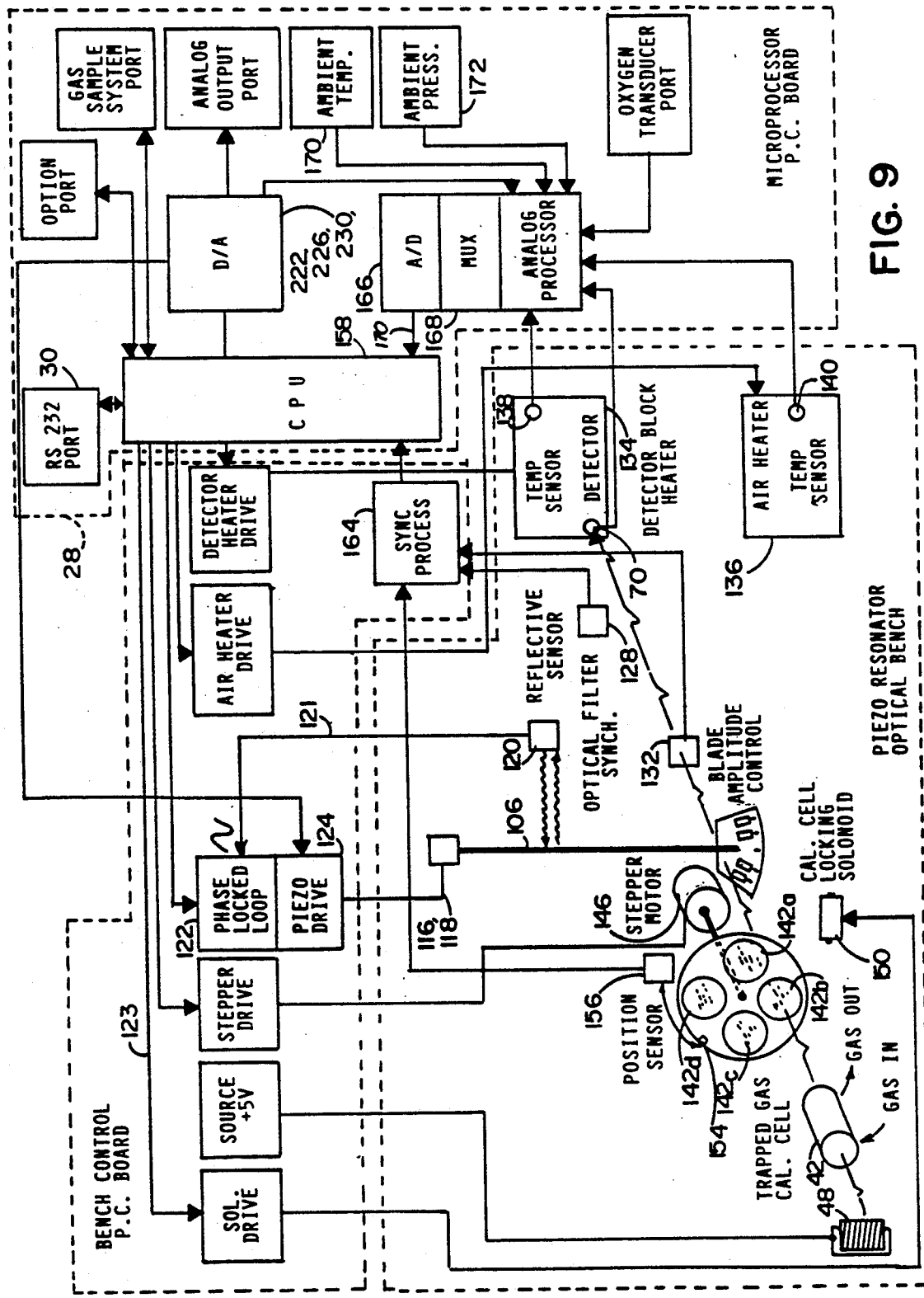
FIG. 9 is a block diagram of the electrical control for a gas analyzer system.

The signals on lines 116, 118 are provided as part of a phase-locked loop (FIG. 9) including an optical reflective sensor 120 mounted on sync-sensor board 90 and which generates an output signal on line 123 that varies with the movement of PE blade 106. The signal on line 123 is received by a phase-lock loop circuit 122 which produces a signal that is amplified by a piezo-drive output stage 124 for providing a nominal 200 volt sine wave of the form illustrated at the top of FIG. 11. An optical emitter 130 on synchronizing source board 90 provides a beam received by a receiver 132 on sync-detector board 92 to produce a pulse when filter carrier 110 clears its path indicating the end of each swing of the filter carrier. The purpose of the end-of-swing pulse is to provide an input to a central processing unit 158 which produces an analog amplitude control signal on line 123 provided to piezo drive 124 in order to control the amplitude of swing of PE block 106. In the illustrated embodiment, phase-lock loop circuit 122 is a commercially available integrated circuit having Model No. CD4046B. A second optical emitter 126 directs a beam through openings 114 which is received by a detector 128 on sync-detector board 92 to provide indexing pulses to indicate the movement of filters 112 through the radiation path.

A detector block heater 134, positioned on support member 94, and air heater 136, positioned on sync-sensor board 90, are regulated respectively by temperature sensors 138, 140 to maintain the temperature of the components within receiver module housing 62, and their surrounding atmosphere, at a constant 55° C. The thermal mass provided by metallic sheet 100 on support 94 additionally serves to stabilize the temperature of the detector subassembly components. It has been found that, because the piezoelectric chopper assembly eliminates the need for a motor to rotate a conventional rotary filter assembly, the components of the detector subassembly can be maintained in a sealed enclosure because no substantial heat-generating components are present to overheat the enclosure. The heaters allow this enclosure to be maintained at a constant temperature. This arrangement temperature-stabilizes all of the most temperature-sensitive components of optical unit 22. In a preferred embodiment, heaters 134, 136 are serpentine-printed circuit heaters.

Calibration assembly 72 includes a plurality of calibration cells 142$a$–142$d$ mounted to a wheel 144, which is rotated by stepper motor 146. When wheel 144 is stationary, solenoid 150 is deenergized so that stopping arm 152 prevents wheel 144 from rotating. This arrangement allows all electrical signals to be removed from stepper motor 146 when it is not being rotated, without concern for drift of the position of wheel 144, in order to reduce the electrical noise in the system. This improves performance because stepper motor 146 is never rotated while any measurements are being taken. A magnet 154 on wheel 144 provides an indication in a Hall-effect sensor 156 to produce a synchronizing signal to identify the location of individual cells 142. Calibration cells 142$a$–142$d$ may contain an amount of a gas that is nonabsorbent to IR radiation in the radiation bands of the component gases, such as nitrogen. Each cell 142$a$–142$d$ may additionally include a trace amount of a tracer gas, such as helium, to provide for the detection of any cell leakage during the manufacturing process. One of the cells 142$a$–142$d$ contains only these two gases and provides a neutral cell which is positioned in the radiation path during the analysis of a sample gas. The remaining calibration cells 142$b$–142$d$ contain one or more of the component gases to be measured in predetermined concentrations and at predetermined pressures. This allows the optical bench unit 22 to be calibrated without requiring the use of bottles of calibration gas for filling the sample chamber with such calibration gases during every calibration routine. The balance of the contents of the cells that contain component gases may include a neutral gas, such as nitrogen, in order to bring the total to 100%.

In order to utilize calibration cells containing concentrations of the components gases to be measured, it is necessary to compensate for the differences in absorption resulting from the differences in radiation path lengths through sample chamber 42 and through cells 142 more specifically, the conventional calibration technique of filling the sample chamber with a calibration gas of known concentration and adjusting the gain of the detection means in order to span-calibrate the analyzer, relies on the fact that the path traveled through the calibration gas is identical with that traveled through a sample gas because both gases are provided separately in the same sample chamber. When the present system is calibrated using the calibration cells, the sample chamber is, instead, filled with a gas that is nonabsorbent of radiation at the bands of the component gases, such as air or nitrogen, and individual calibration cells 142 are rotated seriatim into position in the radiation path. In order to absorb the same amount of radiation at the absorption frequency of each component gas as a gas filling the sample chamber, the concentration of the gas in the calibration cell must be increased to compensate for the significantly shorter radiation path through the cell. This can be accomplished by increasing the concentration of the component gas in the calibration cells in proportion to the ratio between the path length of the sample chamber and the path length through the calibration cell. However, in order to perform a two-point calibration for three gases it is usually not possible to accommodate two samples of each gas, at different concentrations, in the three non-neutral cells using this formulation. The reason is that the sum of the gas concentrations would exceed 100% for at least one cell. This difficulty is overcome by increasing the gas pressure selectively in order to increase the amount of absorption relative to the concentration of each gas in the particular cell. The increase in pressure above atmosphere may be readily determined. For example, if it is determined that the required concentration for HC is 3.63% and that for CO is 121%, then (using 2% helium) three relationships are known:

$$CO+HC\ 98\% \quad (1)$$

$$CO\ P=121\% \quad (2)$$

$$HC\ P=3.63\% \quad (3)$$

By solving these three equations for P, it can be determined that the required pressure in the calibration cell is 1.27 atmospheres and the concentrations are 95.1% CO and 2.85% HC.

As an example, a two-point calibration at 20% full scale and 60% full scale for HC, CO and $CO_2$ requires four calibration cells having the concentration and pressures listed in Table I. The balance of 2% in each cell is helium.

TABLE I

| Cell | Pressure (Atm.) | $N_2$ (%) | HC (%) | CO (%) | $CO_2$ (%) |
|---|---|---|---|---|---|
| 142a | 1 | 98 | 0 | 0 | 0 |
| 142b | 2 | 24.3 | 0.32 | 10.51 | 62.88 |
| 142c | 1 | 11.71 | 2.52 | 85.77 | 0 |
| 142d | 3.3 | 14.19 | 0 | 0 | 83.79 |

In the above example, the sample chamber had a length of 10 cm and each calibration cell had a length of 0.33 cm. The 100% span values for the gas channels are as follows:
HC: 2000 ppm.
CO: 10 percent
$CO_2$: 20 percent Microprocessor unit 28 includes an eight bit central processing unit, or CPU, 158 which is capable of communication with a host computer through serial port 30. This allows the host computer (not shown) to adapt the functions of system 20 to the particular application. For example, calibration curves, to which the present unit may be calibrated at two points for each gas channel, may be entered through port 30 and stored in a random access memory, or RAM 160. Information of a more permanent nature, such as data from a factory calibration performed on system 20, is stored in an EEPROM 162, which is non-volatile, i.e., the data is retained even when power is removed from the system. CPU 158 additionally receives interrupt commands from a synchronizing process circuit 164, including a sample pulse detector 128 which detects the movement of openings 14 and an end-of-swing detector 132 which detects each cycle of filter carrier 110. CPU 158 additionally receives digital inputs from an analog-to-digital converter (A/D) 166.

A/D converter 166 receives time-multiplexed analog signals from a multiplexer 168, which receives various analog inputs, such as from temperature sensors 138, 140 and ambient temperature and pressure sensors 170, 172. In addition, multiplexer 168 receives an analog detector output signal originating from radiation detector and preamplifier 69, which is already time-multiplexed as a result of the operation of chopper assembly 68 placing the optical filters seriatim in the radiation path. Because the output from the radiation detector is time-multiplexed and, as will be set forth in more detail below, is corrected for gain and offset errors without demultiplexing the detector output, the purpose of multiplexer 168 is to multiplex the various continuous analog signals into appropriate time slots in the time-multiplexed analog signal provided to A/D converter 166. The output from A/D converter 166 is provided to CPU 158 in digital format on a bus 170.

Figure 10:
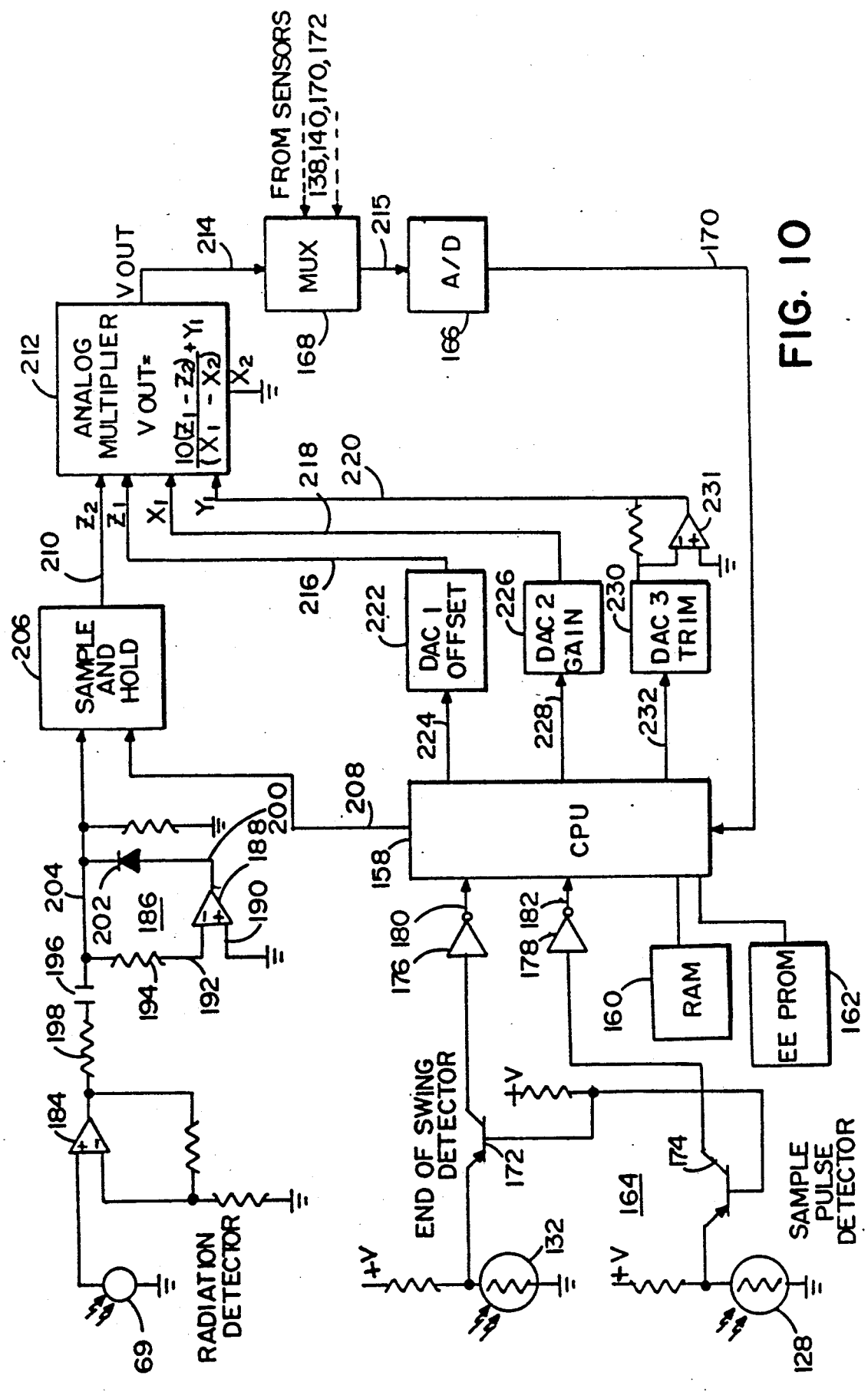
FIG. 10 is a schematic diagram of the radiation detector output processing circuit of the control assembly.

By reference to FIG. 10, the output of sample pulse detector 128 is buffered by common base transistor 174 and invertor 178 and provided as an interrupt generating input 182 to CPU 158. The output of end-of-swing detector 132 is likewise buffered by a common base transistor 172 and inverter 176 and provided as an interrupt generating input 180 to CPU 158. The output of radiation detector and preamplifier assembly 69 is amplified by linear amplifier 184 The output of amplifier 184 is connected through a resistor 198 and capacitor 196 to a line 204. Line 204 is referenced to signal ground by ground clamp circuit 186. Ground clamp circuit 186 includes an operational amplifier 188 whose noninverting input 190 is connected with signal ground and whose inverting input 192 is connected through resistor 194 to line 204. Output 200 of amplifier 188 is connected through a forwardly-poled diode 202 to line 204, which connects capacitor 196 to a sample and hold circuit 206. With this configuration, amplifier 188 will reference the signal on line 204 to the lowest extent of its movement during each cycle of the PE chopper blade, which occurs when the "dark" window, in which no radiation is allowed to pass, is positioned in the radiation path. Sample and hold circuit 206 responds to a trigger signal on line 208 from CPU 158 by retaining the analog value from line 204 on its output line 210 until the next trigger signal is received on line 208.

An analog multiplier 212 is provided which produces an analog output $V_{out}$ on a line 214 according to the following transfer function:

$$V_{out}=[(Z_1-Z_2)/(X_1-X_2)]+Y_1$$

where $X_1$, $Y_1$, $Z_1$ and $Z_2$ are inputs. $X_2$ is also an input but is tied to signal ground which removes it from the formulation of output $V_{out}$. Inputs $Z_1$, $X_1$ and $Y_1$ are provided, respectively, on lines 216, 218 and 220. An analog signal on line 216 is provided from the output of a digital-to-analog converter 222 (DAC1) which receives a digital input on bus 224 from CPU 158. An analog signal on line 218 is provided from an output of a digital-to-analog converter 226 (DAC2) which receives a digital input on bus 228 from CPU 158. Line 220 is provided with an analog signal from an inverting amplifier 231 which inverts and amplifies by a factor of 2 the output of a digital-to-analog converter 230 (DAC3). DAC3 receives a digital input from CPU 158 on bus 232. Input $Z_2$ to analog multiplier 212 is provided on line 210 as the output from sample and hold circuit 206. Output $V_{out}$ is provided on line 214 as an input to multiplexer 168. An output 215 of multiplexer 168 is provided as an input to A/D converter 166, whose output 70 is provided as a digital input to CPU 158. As previously set forth, multiplexer 168 interleaves other analog input signals, not shown in FIG. 10, into available time slots in the time-multiplexed signal on line 214. In the illustrated embodiment, analog multiplier 212 is a commercially available integrated circuit sold by Burr-Brown Corporation under Model MPY634, with an additionally provided input $Y_2$ connected with the analog output terminal $V_{out}$.

Figure 11:
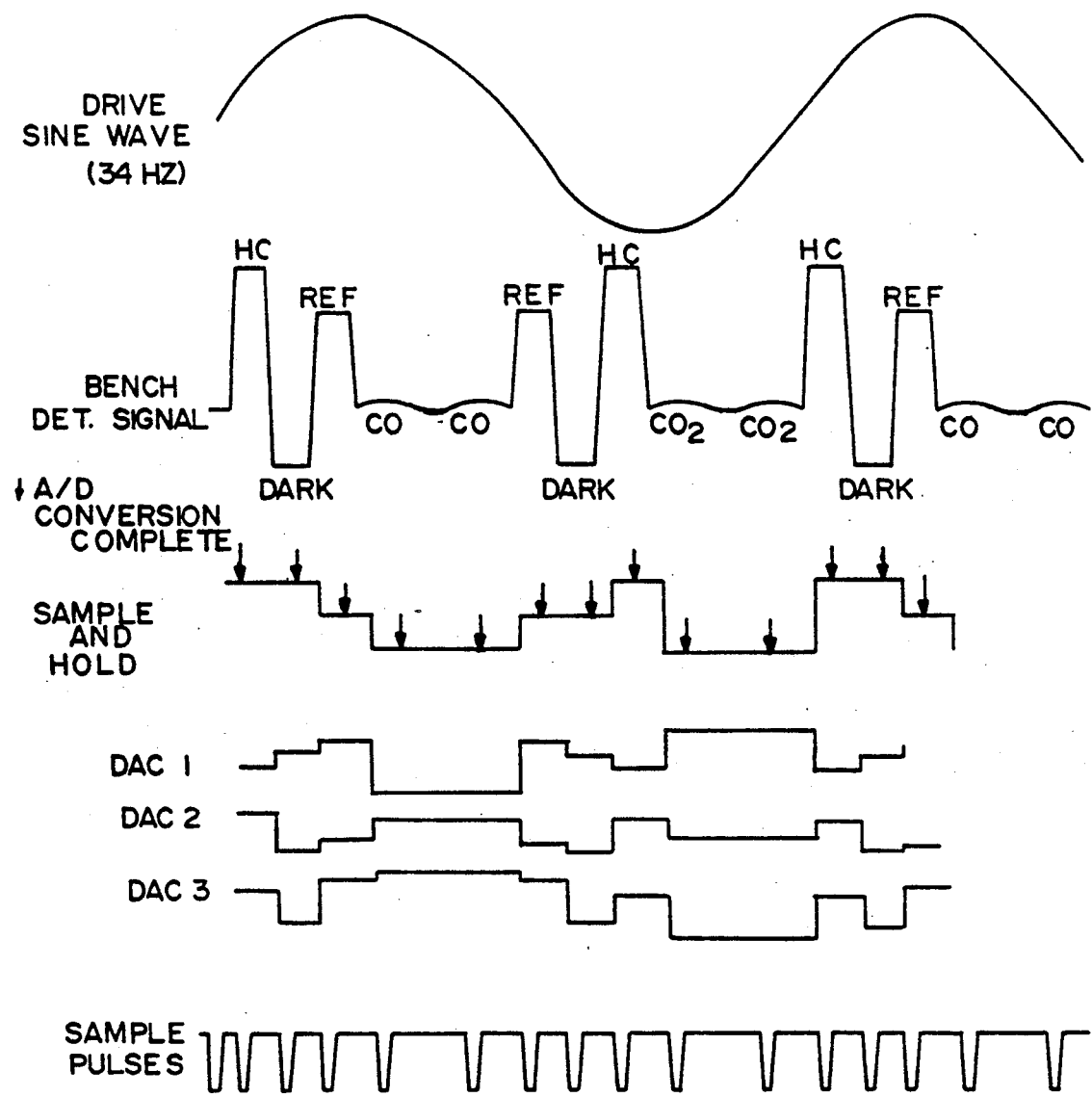
FIG. 11 is a signal diagram illustrating signals for the circuit in FIG. 10.

Operation of infrared gas analyzer system 20 can be understood by reference to FIG. 11 in which the oscillating movement of piezoelectric blade 106 may be visualized by reference to the drive signal applied from drive circuit 124. As blade 106 oscillates, the arcuate movement of filter carrier 110 positions in the radiation path, seriatim, filters which transmit radiation at the absorption band for CO, $CO_2$ and HC. In addition, a REF filter provides a reference reading and a dark portion passes no radiation. The purpose of the dark portion is to produce a "ground" reference level which is clamped to ground by ground clamp circuit 186. The purpose of the reference filter is to allow the system to calculate, and continuously update on a running average basis, an automatic gain control factor (AGC) which is applied to all gas channels to compensate for variations in the intensity of source 48. The output of the sample and hold circuit is illustrated as a DC signal which varies in stepwise fashion The sample pulses received from detector 128 and the synchronizing pulses received from end-of-swing detector 132 provide interrupt commands to CPU 158. The stream of sample pulses indicate that a different filter is positioned in the radiation path and the synchronizing pulse (not shown) provides a reset pulse once each swing of the filter carrier to allow the CPU to identify each particular filter.

For each level of output from detector 70 when a particular filter is positioned in the radiation path, hereafter referred to as a gas channel, an appropriate value of a coarse offset number (offset), a fine offset number (trim) and a gain are stored in RAM 60 and EEPROM 162 that, when applied to analog multiplier 212 coincidentally with receipt of the output 210 from sample and hold circuit 206 for the particular gas channel, will provide a proper zero reference and span calibration for that gas channel. It is to be understood that, although reference is made to various gas channels, in fact, only one electrical "channel" is provided. The electrical "channel" carries a single time-multiplexed signal for all "gas channels."

When CPU 158 receives a sample pulse on interrupt input 182, three numbers are retrieved from tables in RAM 160, EEPROM 162 and simultaneously applied respectively to DAC1, DAC2 and DAC3. The retrieved "offset" number is applied to DAC1, whose output is provided as input $Z_1$ to circuit 212. The retrieved "gain" number is applied to DAC2, whose output is provided as input $X_1$ to multiplier 212. The retrieved "trim" number is applied to DAC3, whose output is inverted by amplifier 231 and provided as input $Y_1$ to multiplier 212. Analog multiplier 212 will respond to these inputs, including the $Z_2$ input from the sampled hold circuit, by producing an analog output $V_{out}$ that will subtract the analog equivalent of the stored "offset" number from the $Z_2$ input received from the sample and hold circuit to compensate for coarse DC offset. Circuit 212 will additionally divide this result by the analog equivalent of the stored gain number to compensate for span variations. Finally, an analog equivalent of the trim value will be subtracted from this result to accomplish fine offset adjustments. Subtraction rather than addition of the offset term results from inversion of the output of DAC3 provided by inverting amplifier 231. The resulting analog signal $V_{out}$ is converted by A/D converter 166 to digital form and provided to CPU 158 as a calibrated, or corrected, signal.

The adjustment to the output of sample and hold circuit 206 for each gas channel and conversion to digital format by A/D converter 166, which occurs at the arrows in FIG. 11, takes place while the filter for that gas channel is in the radiation path, and is complete before the next gas channel is read. Therefore, the output of the absorption detector 70 is fully adjusted for offset and span errors without demultiplexing the time-multiplexed signal. This "on-the-fly" adjustment provides an enormous increase in speed, which allows a large number of samples to be averaged in order to produce a single set of component gas concentration values.

Figure 12:
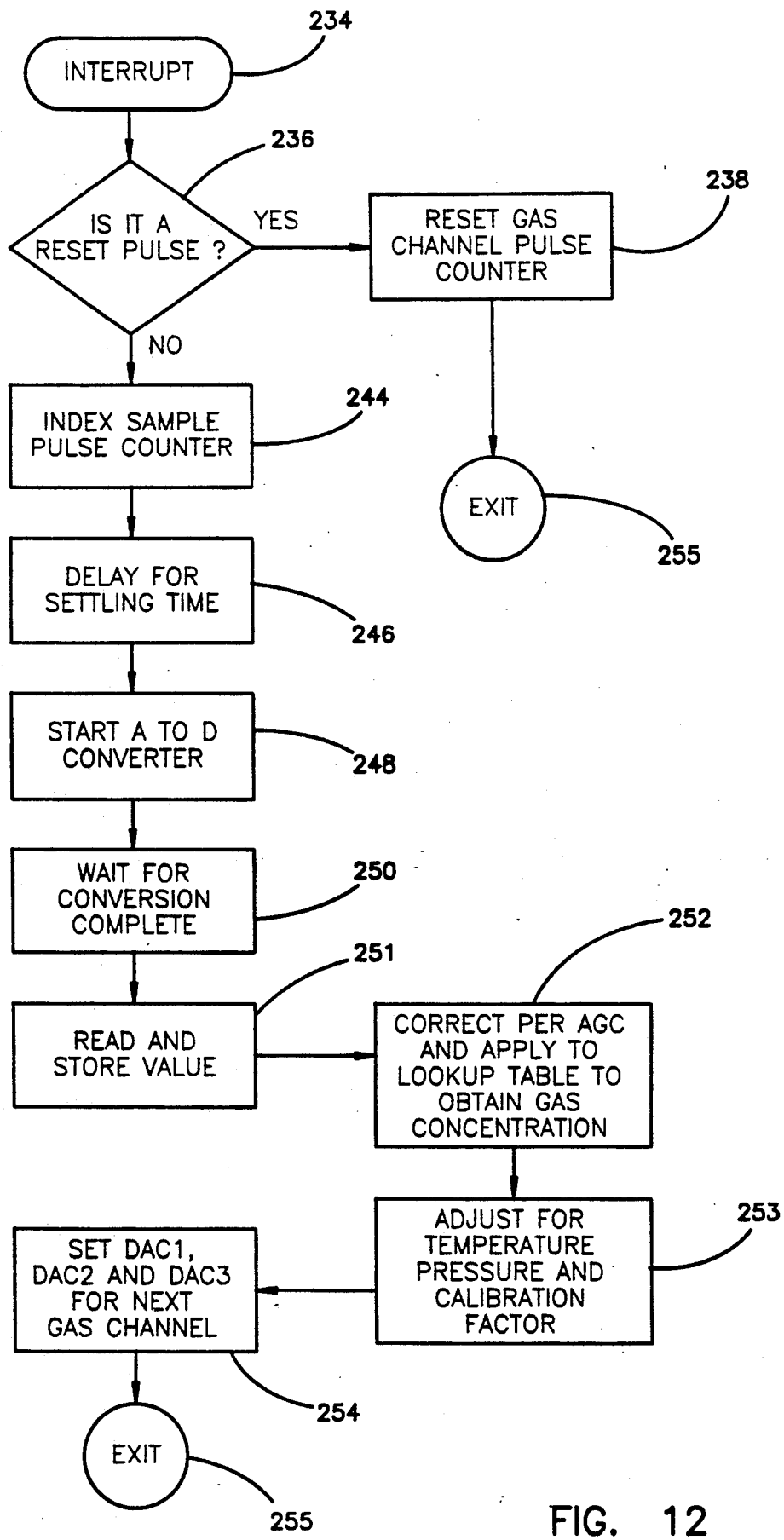
FIG. 12 is a flow chart of the gas concentration measurement routine.
Figure 13:
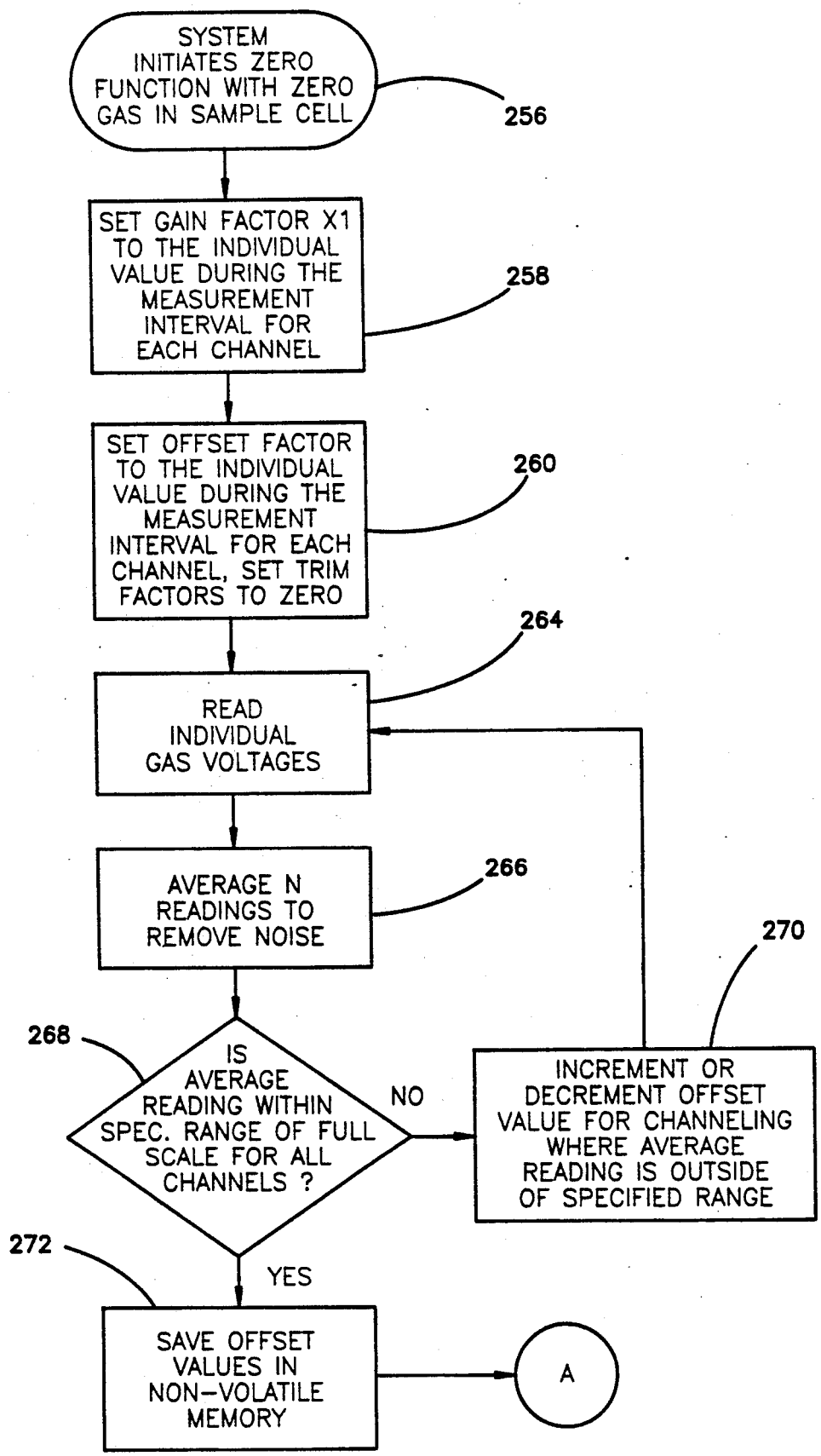
FIG. 13 is a flow chart of the offset routine.

The program for this routine of reading each gas channel may be understood by reference to FIG. 12. When CPU 158 receives (234) an interrupt signal, it is determined at 236 whether the interrupt is a synchronizing, or reset, pulse generated by end-of-swing detector 132 or a sample pulse generated by sample pulse detector 128. If it is determined at 236 that it is a reset pulse that generated the interrupt, then a pulse counter internal to the CPU is reset (238) and the interrupt routine is exited at 255 to await the next interrupt signal. If it is determined at 236 that the interrupt was not generated by a reset pulse then the sample pulse counter is indexed (244) and control passes to block 246. At block 246 a delay is provided to allow the output $V_{out}$ from analog multiplier 212 to settle. After this brief delay, A/D converter 166 is started (248) and, after a waiting period (250), the digital output on line 170 is received (251) by CPU 158 as a gas channel reading. The CPU corrects the gas reading in proportion to the AGC term and applies (252) the gas reading to a lookup table in a semi-permanent storage device such as EEPROM 162 or an EPROM (not shown) to determine a corresponding gas concentration for that gas channel. The concentration is then adjusted (253) on the basis of the ambient temperature and pressure, as determined from sensors 170, 172, and according to a software calibration factor determined during the most recent calibration of the system, whether by calibration gas or by using calibration cells. Control passes to block 254 where the DAC1-DAC3 values for the next gas channel are retrieved from memory before the routine is exited at 255. This routine is preferably repeated N times for each gas channel in order to reduce transient noise from the measurement. Each gas channel measurement is typically averaged for at least 100 readings in less than 4 seconds.

In order to carry out the above gas component concentration measurement, it is necessary to know the proper values of $X_1$, $Y_1$ and $Z_1$ to apply to analog multiplier 212 from CPU 158 for each gas channel. Determination of the gain factor $X_1$ will be set forth in detail during the discussion of the factory calibration routine. The immediate explanation is of the determination of the value of $Z_1$, the offset or coarse offset adjustment term, and $Y_1$ the trim or fine offset adjustment term. With the sample chamber filled with a gas that is nonabsorbent of radiant energy in the band of component gases to be measured, such as air or nitrogen, the zero function is initiated (256). The zero function may be called up according to known criteria, such as upon initial warm-up of the equipment, after a given amount of equipment operation time or other factors known to the skilled artisan. This function sets (258) gain factor $X_1$ to the individual value determined during factory calibration during the interval for each channel. The control then sets (266) the offset factor $Z_1$ to its most recently-determined value during the measurement interval for each channel and sets the trim factor $Y_1$ to zero for all intervals. The control then reads (264) the output $V_{out}$ of analog multiplier 212 to measure the analog output for each channel. Because the $Y_1$ input to analog multiplier 212 is set to zero and the offset input $Z_1$ is set to the most recent value, the output on line 214 is a result of offset voltage provided to input $Z_2$ of analog multiplier 212 corrected by existing offset value $Z_1$. Several readings are taken (266) in order to reduce transient noise and it is determined at 268 whether the average value of $V_{out}$ determined for each gas channel is at least 25% of full scale but not greater than 75% of full scale. For each reference channel the specified acceptable range is 50% to 90% of full scale. If $V_{out}$ is not between 25% and 75% of full scale for all gas channels, and between 50% and 90% of full scale for the reference channel, the routine proceeds to block 270 where the offset term for the channels that are below the specified range are incremented and the offset term for the channels that are above the specified range are decremented. The adjusted offset term is then applied to the $Z_1$ input through DAC1. The output $V_{out}$ for all gas channels is then measured and averaged again (264, 266).

Figure 14:
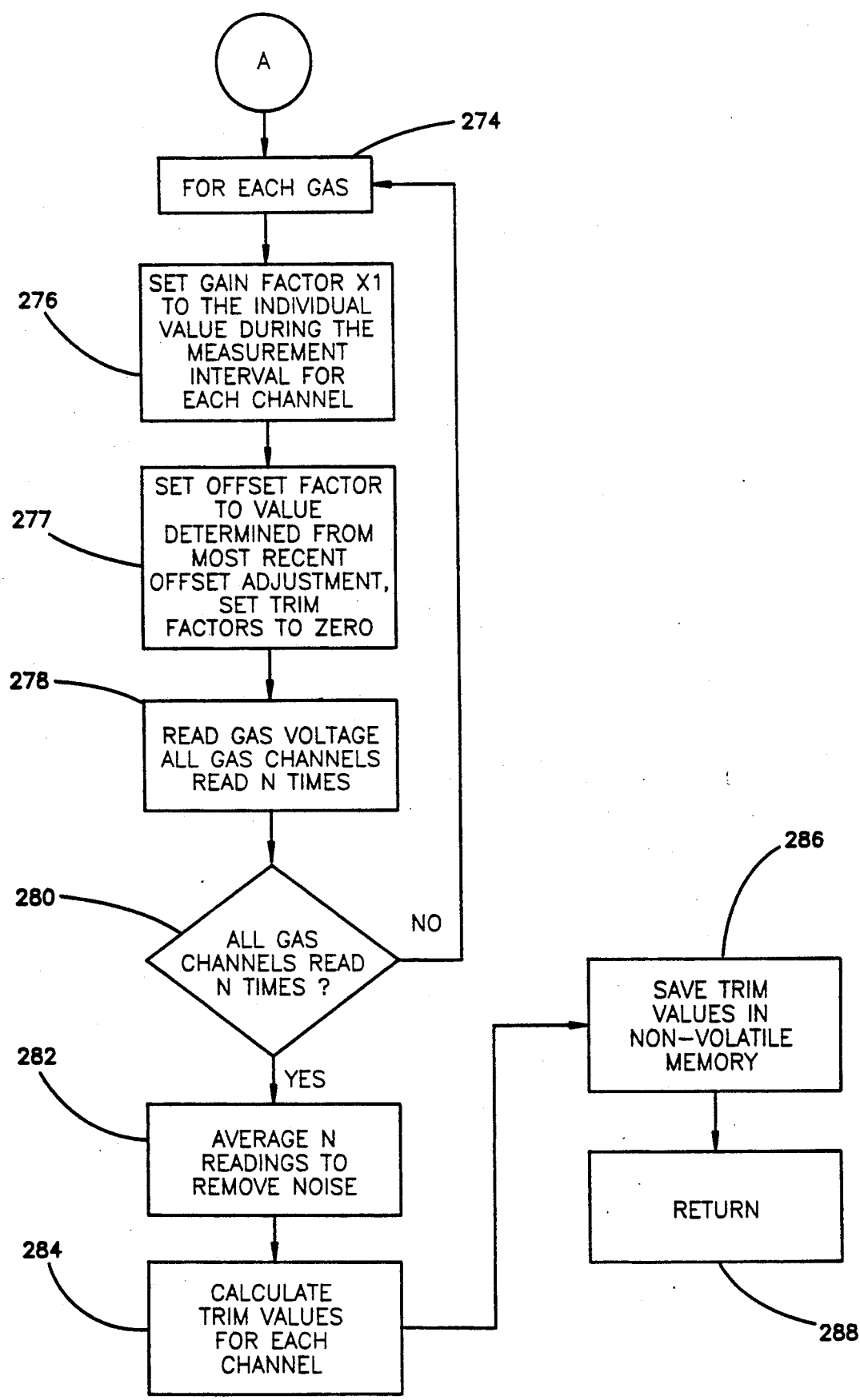
FIG. 14 is a flow chart of the trim routine.

The purpose of assuring that the offset values are at least 25% of full scale is because the trim function is capable of only reducing the value of $V_{out}$. Additionally, the range of outputs from $V_{out}$ is defined between $-4.5$ volts and $+4.5$ volts which is just less than the full range of $-5$ volts to $+5$ volts of A/D converter 166. Thus, it is necessary to produce a sufficiently large offset value, for use in the subsequent trim operation, to assure that the resulting adjustment to the particular gas channel begins at a value that is no less than $-4.5$ volts. The upper offset limit of 75% for gas channels is selected to avoid a "saturated" output condition. The range of 50%–90% for the reference channel is chosen because the reference channel is intended to operate at the midpoint of $V_{out}$, which is 0.0 volts. Because the subsequent trim operation can only subtract, the lower range for the reference channel value of $V_{out}$ is limited during offset routine to positive voltages. Steps 264 through 270 are repeated until all offset values are within their specified range. Control then passes to block 272 where the determined offset values are stored in non-volatile memory and to 274 for performance of the trim routine (FIG. 14).

Because the offset operation is subject to the gain $X_1$ of analog multiplier 212, it can only provide a "coarse" adjustment because any difference between the output of the sample and hold circuit $Z_2$ and the offset term $Z_1$ is multiplied by the gain term. Accordingly, a subsequent trim operation is provided to determine a "fine" adjustment factor $Y_1$ that is not amplified by the gain of analog multiplier 212. As a result, zeroing to within 40 millivolt is possible. In the trim routine, the gain factor $X_1$, determined during factory calibration, is retrieved for one gas channel from EEPROM 162 (274, 276) and applied to DAC2 at the appropriate time for that gas channel. The offset factor $Z_1$, determined during the most recent offset routine, is retrieved from EEPROM 162 and is applied to DAC1 at the appropriate time. The trim factor $Y_1$ is set to zero for all channels. The output $V_{out}$ from analog multiplier 212 is read (278) and the results are saved in RAM. Control then passes to block 280 where it is determined whether all gas channels have been read N times. If not, control passes to 274 where the next channel is read. When it is determined at 280 that all channels have been read N times, control passes to 282 where the N readings are averaged for each channel and to 284 where the trim value $Y_1$ is calculated. The trim value is equal to a digital number which, when written to DAC3 will obtain the result determined in block 282. Because the desired output $V_{out}$ for each gas channel is $-4.5$ volts and for the reference channel is 0.0 volts, the value of $Y_1$ to produce the required fine adjustment may be readily calculated. Control then passes to 286 where the calculated trim values are stored in EEPROM 162 for subsequent use. Control then returns to the primary program at 288.

Figure 15:
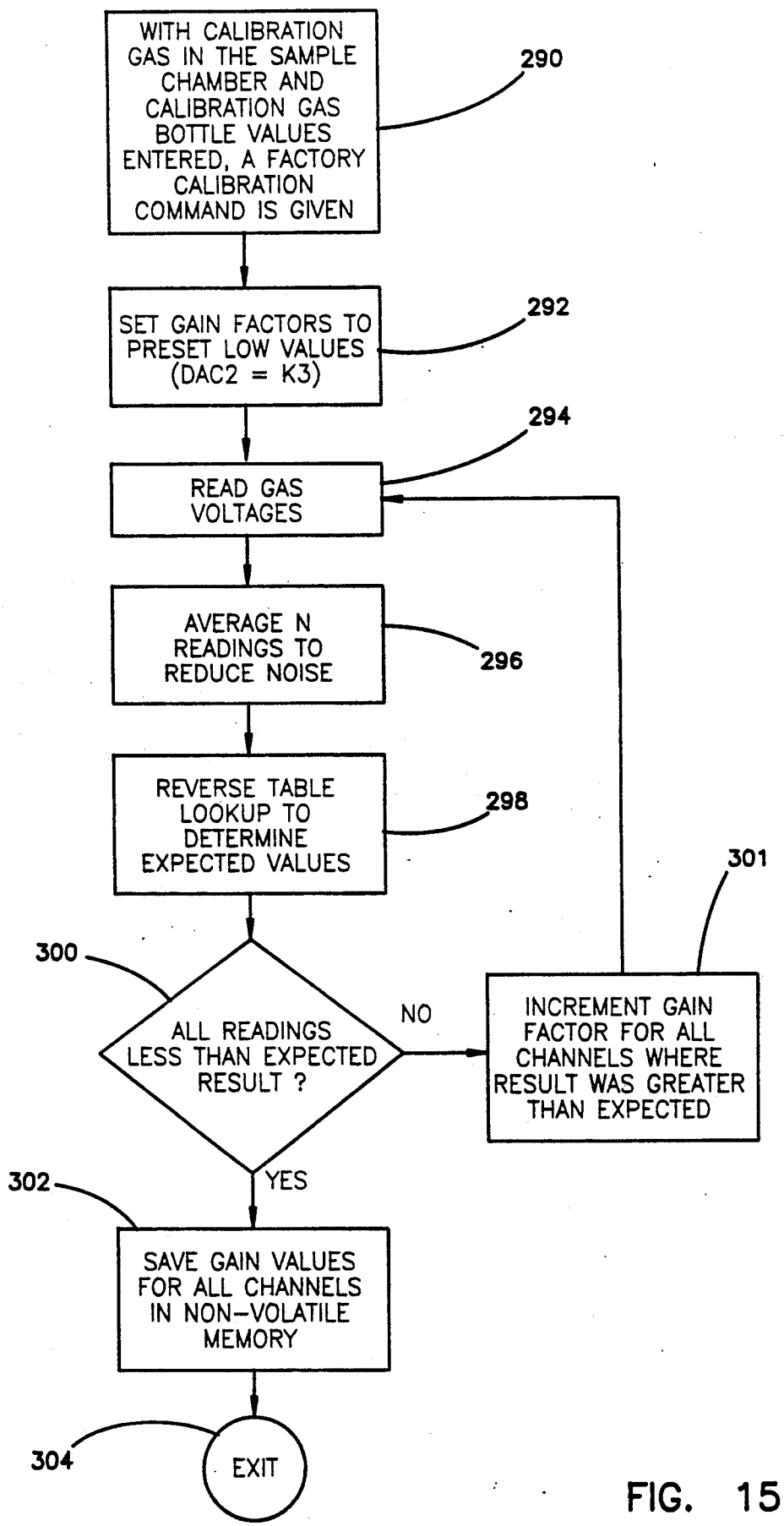
FIG. 15 is a flow chart of the factory calibration routine.

With reference to FIG. 15, the factory calibration routine, which is performed when the system is built or has received a new microprocessor control, begins with a calibration gas filling the sample chamber. The concentration of each component in the calibration gas mixture, which is tagged on calibration gas bottles, is entered in RAM 160. A factory calibration command is given (290) to CPU 158 from a host computer (not shown). The control then sets (292) the gain factor $X_1$ for all gas channels to a preselected low value, which provides a high gain, and with inputs $Z_1$ and $Y_1$ set to values stored during performance of offset and trim routines, the output $V_{out}$ of analog multiplier 212 is read for all gas voltages at 294. An average of N readings of the output of the analog multiplier is made for each gas channel to reduce transient noise. The resulting output values are applied to a reverse lookup table at 298 to determine a gain factor that should produce the readings obtained from the analog multiplier output in response to the composition of the calibration gas. If it is determined at 300 that the readings for all gas channels are less than the results obtained from the lookup table, then these values are written to non-volatile memory such as EEPROM 162 as a calibration factor $X_1$ for each respective channel (302).

On the first pass through this routine, the output from the analog multiplier, as read through the A/D converter 166, should be greater than the expected value from the lookup table, indicating that the gain factor $X_1$ is set too low. If this occurs, as expected, control passes to 301 where the gain factor for all channels, for which the result was greater than expected, is incremented upwardly and steps 294 through 300 are repeated. As this process is repeated, the A/D results for a given gas channel may be lower than the expected value from the lookup table. When this occurs, the gain factor for that channel is saved in non-volatile memory at 302 and is used as gain factor $X_1$ for all subsequent measurements until the factory calibration routine is repeated. After the $X_1$ term has been determined for all channels, the function is exited at 304.

Figure 16:
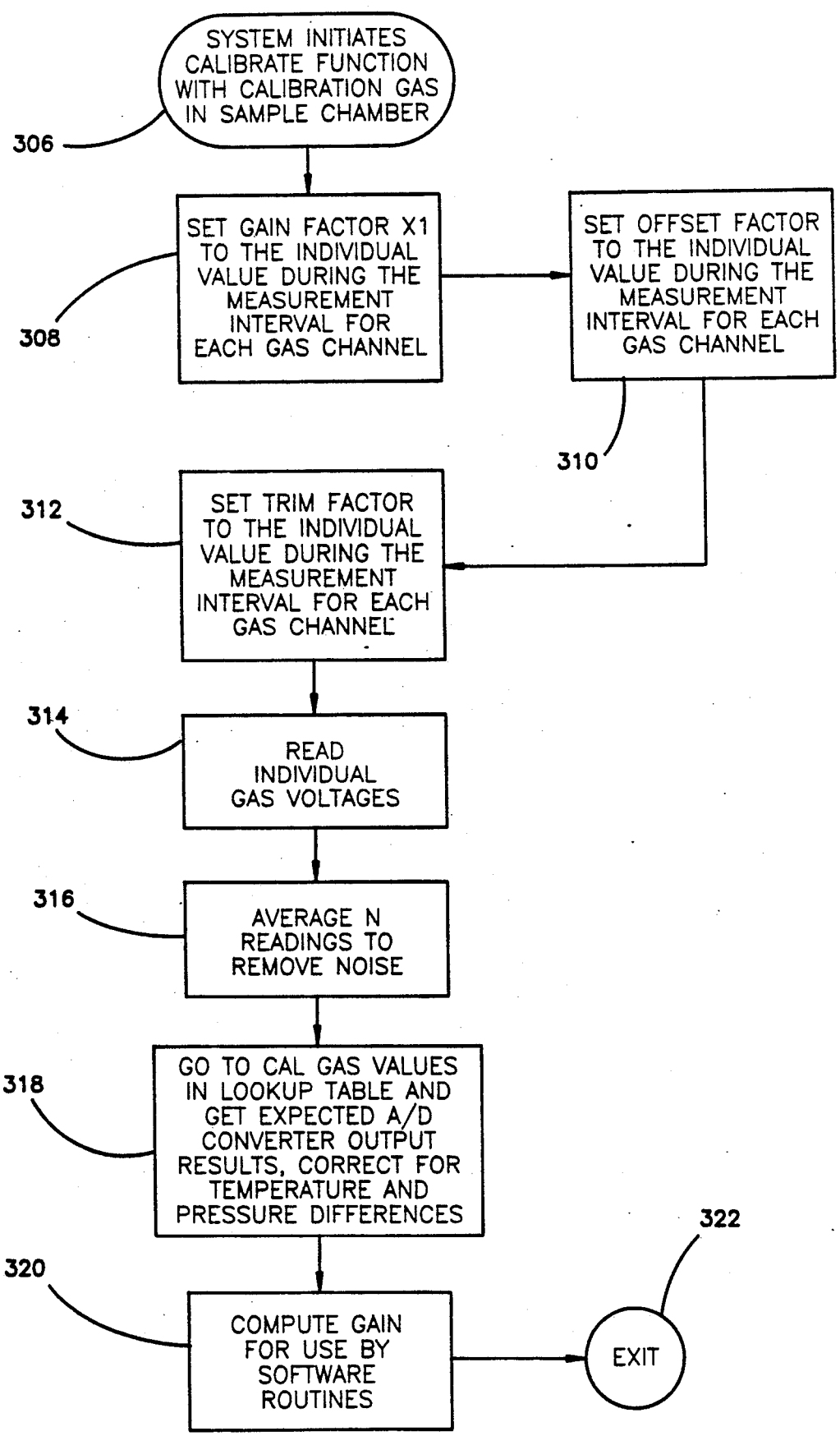
FIG. 16 is a flow chart of the calibration with calibrating gas routine.

Once the factory calibration is performed and the unit is placed in service, provisions are made for two methods of calibrating the span of each gas channel. One method, illustrated in FIG. 16, utilizes calibration gas containing a known mixture of component gases. With the sample chamber filled with a calibration gas and the tag values of the calibration gas entered into RAM 160 from the host computer (306) the gain factor $X_1$ is set (308) to the stored value for each gas during the time-multiplex measurement interval for each particular gas channel, via DAC2 to the $X_1$ input of analog multiplier 212. Likewise, the offset factor $Z_1$ is set (310) to the value stored for each gas value during the appropriate measurement interval for each gas channel via DAC1 to input $Z_1$ of analog multiplier 212. The trim factor is likewise set (312) to the value stored for the gas during the appropriate measurement interval for each gas channel via DAC3 to the $Y_1$ input in analog multiplier 212. The output of A/D converter 166 is saved during the appropriate interval as the corrected value for each gas channel, at 314. A total of N readings are averaged (316) in order to reduce transient noise.

The control applies the tag values of the calibration gas bottles to the lookup table and obtains expected A/D converter output results. The retrieved results are then corrected for temperature and pressure differences between the moment of calibration and the values applied in the lookup table. A software gain factor is then computed at 320 for use by CPU 158 in correcting component gas measurement readings The software gain value, or calibration factor, is computed as the ratio of the value obtained from the lookup table to the measured value. The routine is then exited at 322.

Figure 17:
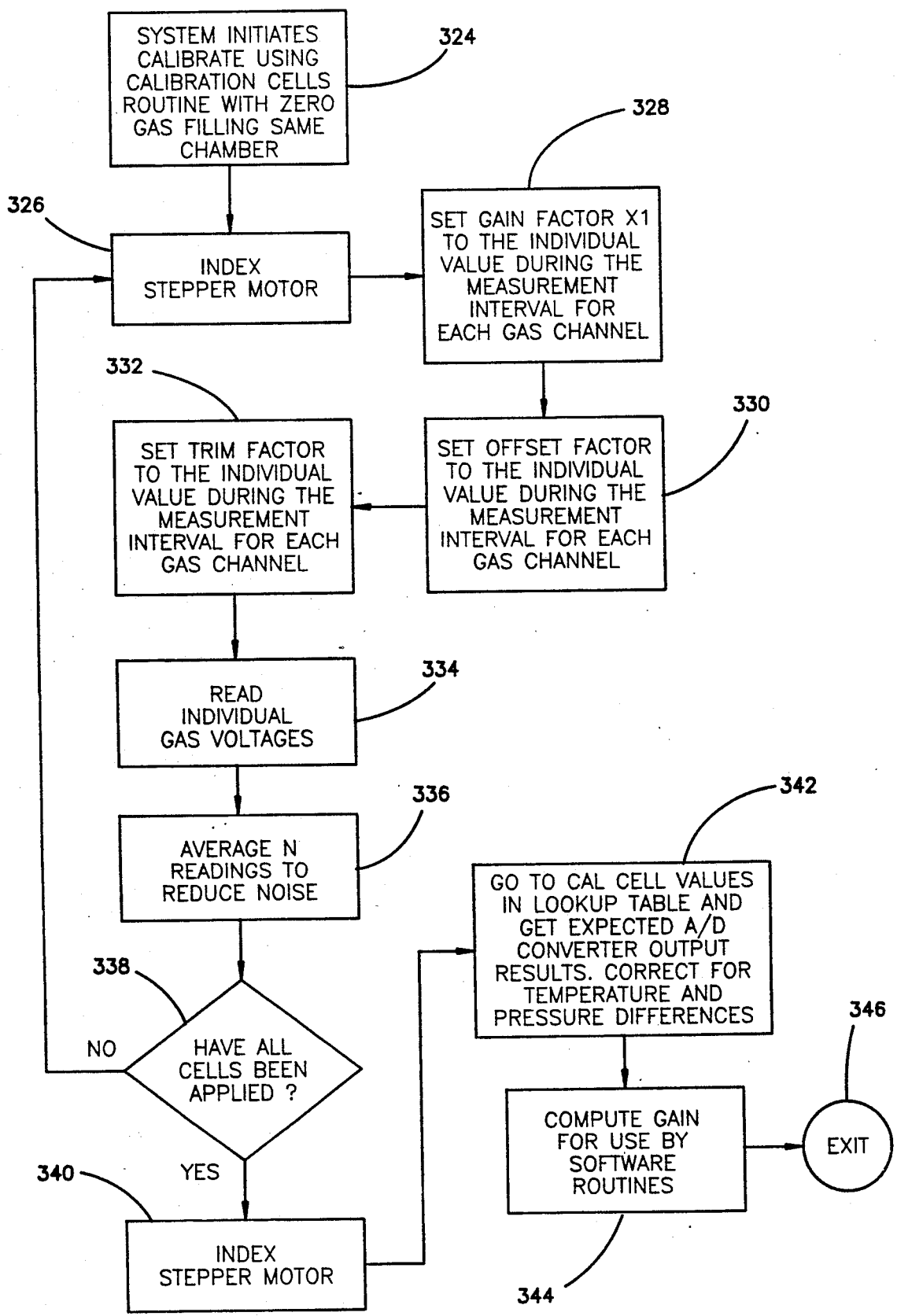
FIG. 17 is a flow chart of the calibration with calibrating cells routine.

A clear disadvantage of the previous function of calibration using a calibrating gas, is the requirement for relatively costly bottles of calibrating gas and the attendant problems of storage, and the like. In order to minimize this difficulty, a calibration using calibration cells routine illustrated in FIG. 17 is provided in order to compute the same software gain, or calibration factor, for use in correcting component gas concentration readings without the use of calibration gas bottles. The calibration using calibration cells routine is initiated at 324 with sample chamber filled with a gas, such as nitrogen or air, that does not absorb radiation at the wavelength of the component gases. Stepper motor 146 is indexed at 326 in order to position one of the cells 142b-142c, which contain one or more component gases, into the radiation path. The gain factors $X_1$, the offset factor $Z_1$ and the trim factor $Y_1$ for each gas channel is applied to analog multiplier 212 during the appropriate measurement interval (328, 330, 332) in the same manner as steps 308-312, and the A/D converter output 170 is read (334). N readings are averaged (326), as during the calibration with calibrating gas routine, and the results are saved (336). It is then determined at 338 results the above procedure has been completed for all calibration cells. If not, control returns to 326 where the stepper motor is indexed to bring the next calibration cell into the radiation path. When it is determined at 338 that all calibration cells containing a component gas have been positioned in the radiation path, the stepper motor is indexed at 340 to bring the neutral cell 142a into the radiation path. Control then passes to block 342 where the readings for each gas channel derived from each calibration cell are applied to an appropriate lookup table to determine an expected A/D converter output result for the particular measurement. If the particular cell does not contain a component for the gas channel, that result is discarded. Separate lookup tables are provided for the expected results at the two calibration points for each gas channel. Control then passes to block 344 where the gain for use in software adjustments is determined as the ratio of the value obtained from the lookup table divided by the measured value for each gas channel. The routine is then exited at 346.

Figure 18:
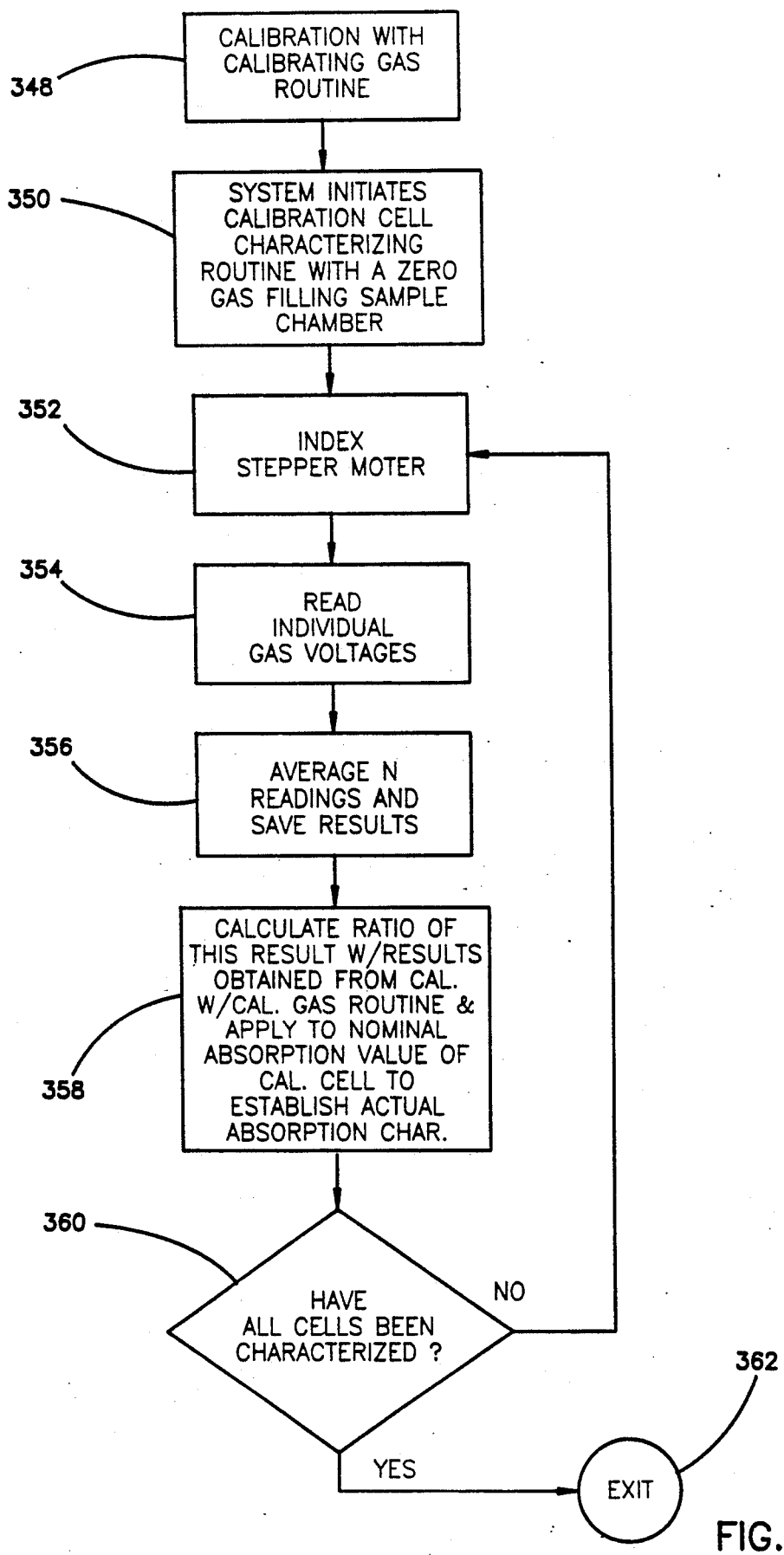
FIG. 18 is a flow chart of the characterizing of calibration cells routine.

The calibration cells 142a-142d are manufactured with a desired gas concentration for various component gases to be measured. The manufacturing process, however, is not accurate enough to provide a gas concentration that is suitable for the precision required in most applications of the gas analyzer system 20. Accordingly, an in situ calibration cell characterizing routine is provided, as illustrated in FIG. 18. After system 20 has been calibrated using calibrating gas at 348, and with a gas that is nonabsorbent of radiation at the wavelength of the component gases filling the sample chamber, the system initiates (35) the characterizing calibrations cells function. Stepper motor 146 is indexed (352) in order to bring the first calibration cell that contains a component gas into the radiation path. With the previously determined components of gain ($X_1$), offset ($Z_1$) and trim ($Y_1$) applied to analog amplifier 212 at the appropriate measurement interval, the output of A/D converter 166 is measured at 354. N such measurements are averaged at 346 and saved. The system then determines the ratio at 358 of the averaged readings for each gas channel at the two calibration points with the corresponding values obtained during the calibration with calibrating gas routine. The ratio is applied to the nominal absorption value of each component gas in the calibration cell to establish the actual absorption characteristic for each component gas in each calibration cell. Suitable adjustments are made for ambient temperature and pressure variations. Control then passes to 360 where it is determined whether all calibration cells have been characterized. If not, control returns to block 352 where the index motor is indexed and the next calibration cell is brought into the radiation path. If it is determined at 350 that all calibration cells have been characterized, then the routine is exited at 362.

The gas analyzer system disclosed herein provides exceptionally accurate and repeatable results. Accordingly, various fault flags may be set, to indicate a failure, when any reading falls outside of an expected range. For example, a ruptured calibration cell may be flagged when a significant mismatch occurs between expected and actual readings. Changes and modifications in the specifically described embodiments can be carried out without departing from the principles of the invention which is intended to be limited only by the scope of the appended claims, as interpreted according to the principles of patent law including the doctrine of equivalents.

The embodiments of the invention in which an exclusive property or privilege is claimed are defined as follows.

1. An apparatus for detecting a component as in a sample comprising:
    a sample chamber for containing a sample gas including the component gas to be detected;
    source means for directing infrared radiation through the sample chamber in a preselected spectral band;
    detector means responsive to radiation incident thereon in the preselected spectral band passing through the sample chamber from the source means for producing a detector output;
    signal processing means responsive to said detector output for indicating the relative concentration of the component gas to be detected, said signal processing means including a circuit having first and second inputs and adapted to producing a difference output that is the difference between a signal provided to said first input and a signal provided to said second input;

first means for concurrently applying said detector output to said first input and a zero-value signal to said second input with substantially nonabsorbent gas filling the sample chamber to produce an offset value on said difference output;

second means for concurrently applying both said detector output to said first input and said offset value to said second input with a sample gas including a component gas to be detected filling said sample chamber thereby producing a difference output that indicates the relative concentration of said component gas.

2. The apparatus in claim 1 in which said circuit further includes a third input and in which said difference output is the sum of a signal applied to said third input and said difference between a signal provided to said first input and a signal provided to said second input.

3. An apparatus for detecting a component gas in a sample comprising:

a sample chamber for containing a sample gas including the component gas to be detected;

source means for directing infrared radiation through the sample chamber in a preselected spectral band;

detector means responsive to radiation incident thereon in the preselected spectral band passing through the sample chamber from the source means for producing a detector output;

signal processing means responsive to said detector output for indicating the relative concentration of the component gas to be detected, said signal processing means including a circuit having first, second and third inputs and adapted to producing a difference output that is the sum of a signal applied to said third input and the difference between a signal provided to said first input and a signal provided to said second input;

first means for applying said detector output to said first output and a zero-value signal to said second input with substantially nonabsorbent gas filling the sample chamber to produce an offset value on said difference output;

second means for applying said detector output to said first input and said offset value to said second input with a sample gas including a component gas to be detected filling said sample chamber thereby producing a difference output that indicates the relative concentration of said component gas;

third means for applying said detector output to said first input and said offset value to said second input with a substantially nonabsorbent gas filling the sample chamber to produce a trim value on said difference output; and wherein said second means includes means for applying said trim value to said third input.

4. An apparatus for detecting at least one component gas in a sample comprising:

a sample chamber for containing a sample gas including the component gas to be detected;

source means for directing infrared radiation through the sample chamber in a preselected spectral band;

detector means responsive to radiation incident thereon in the preselected spectral band passing through the sample chamber from the source means for producing a detector output;

multiplexing means for applying a plurality of filters during distinct time intervals between said source means and said detector means to time-multiplex said detector output, one of said filters having radiation transmitting characteristics that will provide an indication of the concentration of the component gas to be detected; and a correction circuit adapted to applying at least one correction factor to said detector output to provide a corrected output, said correction circuit being synchronized with said multiplexing means in order to apply a particular said correction factor to said detector output for said component gas to be detected during the interval of time that said one of said filters is between said source means and said detector means.

5. The apparatus in claim 4 in which said correction factor includes values for correcting said output for offset and gain errors.

6. The apparatus in claim 4 in which said correction circuit is responsive to said detector output for providing said corrected output as a difference between said detector output and a first correction factor and as a quotient between said detector output and a second correction factor.

7. The apparatus in claim 6 in which said first correction factor is an offset correction factor and said second correction factor is a gain correction factor.

8. The apparatus in claim 4 in which said correction circuit is further adapted to applying a second particular said correction factor to said detector output for another component gas to be detected during another interval of time that another one of said filters is between said source means and said detector means, said another one of said filters having radiation transmitting characteristics that will provide an indication of the concentration of the another component gas to be detected.

9. A method for detecting at least one component gas in a sample including the steps of:

providing a sample chamber for containing a sample gas including the component gas to be detected;

directing infrared radiation through the sample chamber in a preselected spectral band;

detecting radiation in the preselected spectral band passing through the sample chamber and producing a detector signal;

imposing a plurality of filters during distinct time intervals in the path of radiation to time-multiplex said detector signal, one of said filters having radiation transmitting characteristics that will provide an indication of the concentration of the component gas to be detected; and applying a correction signal to said detector signal in synchronism with said imposing to apply a correction factor to said detector output for said component gas to be detected during the interval of time that said one of said filters is in said path of radiation and thereby providing a corrected detector value.

10. The method in claim 9 in which said step of applying a correction signal includes producing said corrected detector signal as a difference between said detector signal and a first correction factor and as a quotient between said detector signal and a second correction factor.

11. The method in claim 9 in which said first correction factor is an offset correction factor and said second correction factor is a gain correction factor.

12. The method in claim 9 in which said step of applying a correction signal includes:
producing a difference output that is the difference between
said detector signal and an offset value whereby said difference output indicates the relative concentration of said component gas.

13. The method in claim 12 further including the step of producing said offset value by obtaining the difference between said detector signal and a zero-value signal with a substantially nonabsorbent gas filling the sample chamber.

14. The method in claim 12 further including the step of summing a trim value with said difference output.

15. The method in claim 14 further including the step of:
producing said trim value by obtaining the difference between said detector signal and said offset value with a substantially nonabsorbent gas filling the sample chamber.

16. The method in claim 9 in which said step of applying a correction signal includes applying a second correction factor to said detector signal for another component gas to be detected during another interval of time that another one of said filters is in the path of radiation source, said another one of said filters having radiation transmitting characteristics that will provide an indication of the concentration of the another component gas to be detected.

* * * * *

UNITED STATES PATENT AND TRADEMARK OFFICE
CERTIFICATE OF CORRECTION

PATENT NO. : 5,184,017
DATED : February 2, 1993
INVENTOR(S) : Edward L. Tury et al.

It is certified that error appears in the above-indentified patent and that said Letters Patent is hereby corrected as shown below:

Column 3, line 13
After "in FIG." insert --5--;

Column 5, line 41
"With" should be --with--;

Column 6, line 16
After "rotated" insert --in step-wise fashion-- and after "by" insert --a--;

Column 6, line 16
After "motor 146." insert --Stepper motor 146 is mounted to a polymeric support 148 which is, in turn, attached to cover 78. A solenoid 150 retracts a stopping arm 152 whenever wheel 144 is being rotated by stepper motor 146.--;

Column 7, line 67
"14" should be --114--;

Column 8, line 29
After "184" insert --.--;

Column 9, line 5
"output 70" should be --output 170--;

Column 9, line 32
After "fashion" insert --.--;

UNITED STATES PATENT AND TRADEMARK OFFICE
CERTIFICATE OF CORRECTION

PATENT NO. : 5,184,017

DATED : February 2, 1993

INVENTOR(S) : Edward L. Tury et al

It is certified that error appears in the above-indentified patent and that said Letters Patent is hereby corrected as shown below:

Column 13, line 28
After "readings" insert --.--;

Column 13, line 45
"142b-142c" should be --142b-142d--;

Column 13, line 54
Delete "results" and insert --whether--;

Column 14, line 18
"(35)" should be --(350)--;

Column 14, line 57, Claim 1
"as in" should be --gas in--;

Column 15, line 7, Claim 1
After "applying" insert --both--;

Column 15, line 45, claim 3
"output" should be --input--;

Signed and Sealed this

Thirtieth Day of August, 1994

Attest:

BRUCE LEHMAN

Attesting Officer       Commissioner of Patents and Trademarks